US00PP13006P2

(12) United States Plant Patent
Burrows

(10) Patent No.: US PP13,006 P2
(45) Date of Patent: Sep. 24, 2002

(54) HELICHRYSUM PLANT NAMED 'PROSIL'

(76) Inventor: John D. Burrows, 6 Shingay Lane, Sawston, Cambridge, Cb2 4SS (GB)

( * ) Notice: Subject to any disclaimer, the term of this patent is extended or adjusted under 35 U.S.C. 154(b) by 25 days.

(21) Appl. No.: 09/654,366

(22) Filed: Sep. 1, 2000

(51) Int. Cl.[7] ..... A01H 5/00
(52) U.S. Cl. ..... Plt./359

(58) Field of Search ..... Plt./359

*Primary Examiner*—Bruce R. Campell
*Assistant Examiner*—Susan B. McCormick

(57) ABSTRACT

A new cultivar of Helichrysum named 'Prosil' that is characterized by a compact plant habit, fine tightly dense foliage that is vivid silver/pearl in color and insignificant flowers that may only rarely bloom. In combination these traits distinguish 'Prosil' from all other existing varieties.

3 Drawing Sheets

BOTANICAL CLASSIFICATION

*Helichrysum xambiguum.*

Variety Denomination

'Prosil'.

CROSS-REFERENCES TO RELATED APPLICATIONS

This application is related to another application entitled Helichrysum Plant Named 'Prospi', Ser. No. 09/654,532, filed Sep. 1, 2000.

BACKGROUND OF THE INVENTION

The present invention relates to a new and distinct cultivar of *Helichrysum xambiguum* named 'Prosil'. The new plant was bred and selected in 1995 by the inventor in Sawston, Cambridge, Great Britain from seed that originated from unintroduced Helichrysum hybrids. Seedlings were grown out during the spring of 1995 and were selected for vegetative propagation based on a more compact plant habit and finer, denser, more vivid-colored foliage than other known cultivars of this type. The inventors breeding program is designed to enhance the foliage color of Helichrysum from the normal gray or dull green to brighter silver and pearl colors.

'Prosil' is distinguished by a compact plant habit and dense, fine foliage of a vivid silver/pearl color. These combined characteristics distinguish 'Prosil' from all others that exist. In comparison, the only similar plant is Helichrysum 'Prospi', which exhibits a more open in habit and has green and silver foliage rather than silver/pearl foliage. Standard non-patented varieties of *Helichrysum angustifolium* have untidy foliage, dull and greener foliage, broader foliage and regular, significant flowering. Compared to these 'Prosil' has tidy foliage, finer and brighter foliage of a silver/pearl color and insignificant yellow flowers. Although 'Prosil' has reportedly flowered rarely in the UK, the plant has flowered profusely in California during the second year in a 7-gallon container. However, the foliage and habit remain its distinguishing features, as the folowers are insignificant when compared to traditional existing varieties, and subsequent flowering has not been observed. *Helichrysum*

*angustifolium* cultivar 'Dartington' (not patented) is more compact but has darker foliage that is not fine-leaved.

The new cultivar was first asexually propagated in 1996 by the inventor in Rivenhall, Essex, Great Britain. Since that time, the new variety has been repeatedly asexually reproduced by means of cuttings and has been found to remain firmly fixed in subsequent generations as herein disclosed.

SUMMARY OF THE INVENTION

The following traits have been repeatedly observed and represent the characteristics of the new cultivar. These attributes in combination distinguish the new invention from other varieties. Although 'Prosil' is similar in form and habit to 'Prospi', 'Prosil' exhibits a denser form with silver/pearl foliage. Compared to standard non-patented varieties such as *Helichrysum angustifolium,* the new individual 'Prosil' is more compact, tidier with finer foliage of a silver/pearl color, and insignificant flowers that may only rarely flower.

BRIEF DESCRIPTION OF THE DRAWINGS

The accompanying color photographs illustrate the overall appearance of the new cultivar.

Sheet 1 has two photos showing the entire plant and habit, with blooms, from a front perspective.

Sheet 2 shows the entire plant and habit, without flowers.

Sheet 3 compares the foliage color and habit of 'Prosil' on the left with 'Prospi' on the right. All photographs are taken of plants grown in seven-gallon containers. The prints are made using conventional photographic techniques and although foliage colors may appear different from actual colors due to light reflectance, they are as accurate as possible by conventional photography.

BOTANICAL DESCRIPTION OF THE PLANT

The following is a detailed botanical description of the new Helichrysum cultivar 'Prosil'. Observations, measurements, values, and comparisons were collected in Encinitas, Calif. from 2 year old plants grown outdoors under prevailing conditions in seven-gallon containers. The new Helichrysum plant has not been observed under all possible environmental conditions. The phenotype may vary with variations in environment such as temperature and light level, without, however, any variance in genotype. Color references are made to The 1995 Royal Horticultural Society Colour Chart except where general terms of ordinary dictionary significance are used. The growing requirements are similar to the species and no growing problems have been observed.

Botanical classification: Helichrysum 'Prosil'.
Common name: Licorice plant.
Parentage: A hybrid of *Helichrysum xambiguum.*
Propagation: Vegetative cuttings.
Rooting habit and time to develop: 3 weeks to root from cutting; 12 to 16 weeks to reach one-gallon size.
Plant form and growth habit: Compact, mounding.
Type: Biennial/perennial for mixed borders or specimens.
Vigor: Vigorous.
Growth rate: Vigorous growth outdoors with excellent branching. Grows to 20.0 cm height in 20 weeks.
Branching habit: Tightly dense, compact.
Hardiness: Zero degrees Centigrade.
Mature height and spread: 40 cm by 90 cm.
Stem color: 189D and 190D.
Stem shape: Cylindrical.
Stem length: 27 cm.
Stem diameter: 0.25 cm.
Internode length: 1 cm to 1.25 cm.
Stem surface: Sericeous, silky with long appressed hairs.
Foliage:
*Leaf arrangement*.—Alternate.
*Quantity*.—Abundant.
*Shape*.—Linear; narrowly acute.
*Leaf length*.—4 cm.
*Leaf width*.—3 mm to 4 mm.
*Margin type*.—Entire.
*Leaf base*.—Sheathing, cobwebby surface at inside juncture.
*Leaf tip*.—Acute.
*Leaf division*.—Simple.
*Leaf venation*.—Main vein prominent on underside of leaf and depressed on upper surface.
*Vein surface*.—Main vein tomentose.
*Texture*.—Silky.
*Surface*.—Tomentose.
*Upper leaf color* (*mature*).—191B.
*Lower leaf color* (*mature*).—191D.
*Upper leaf color* (*young*).—191B.
*Lower leaf color* (*young* ).—191C.
*Petiole*.—None, semi-amplexicaul.
*Foliar fragrance*.—Sweet, powder-like anise scent.
Flower:
*Inflorescent type*.—Head, flat umbel, 30 to 40 flowers per umbel.
*Umbel dimensions*.—3.50 cm in diameter, 1.50 cm in height.
*Flowering season*.—Spring and summer.
*Flower color*.—9D opening, 13A open.
*Flower size*.—50 cm in diameter; 0.50 cm in height.
*Flower shape*.—Circular.
*Fragrance*.—Licorice scent.
*Aspect*.—Erect, facing upward.
*Petals*.—Numerous, shape ovate, apex obtuse.
*Involucral bracts*.—Hairy, dry, color: yellow-white.
*Inner bracts*.—5.0 mm in length.
*Outer bracts*.—1.25 mm in length.
*Fruit*.—Angled, slightly compressed, hairless capsule.
*Seed*.—Dark brown with white glands.

I claim:

1. A new and distinct cultivar of *Helichrysum xambiguum* plant named 'Prosil' as described and illustrated.

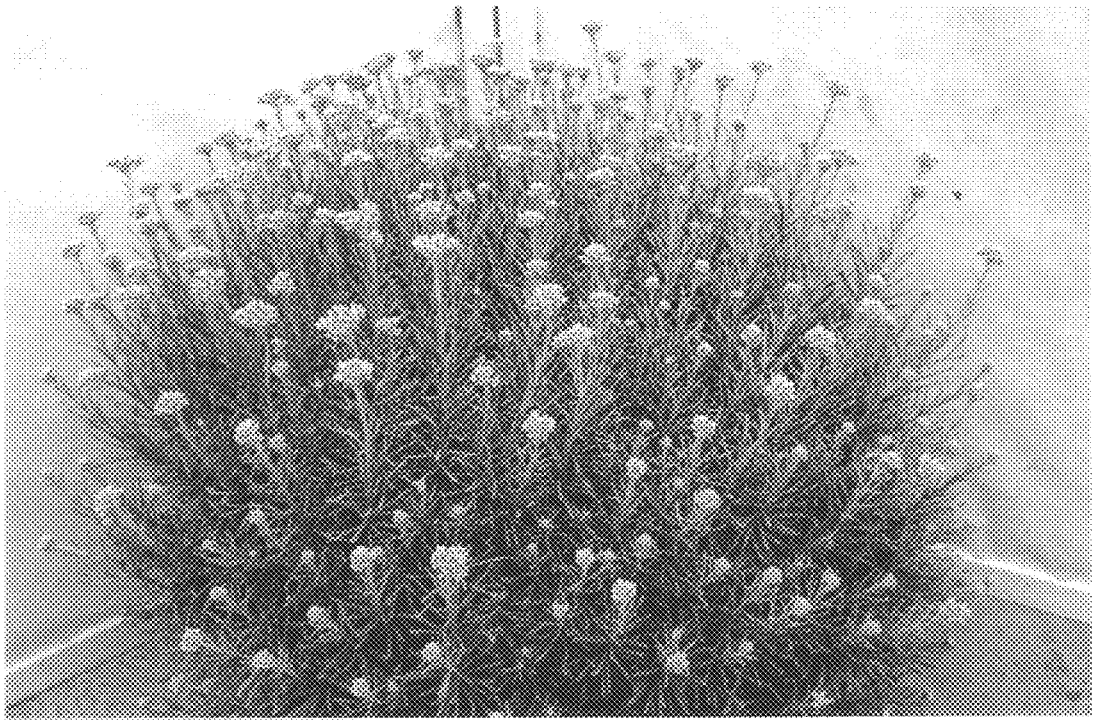
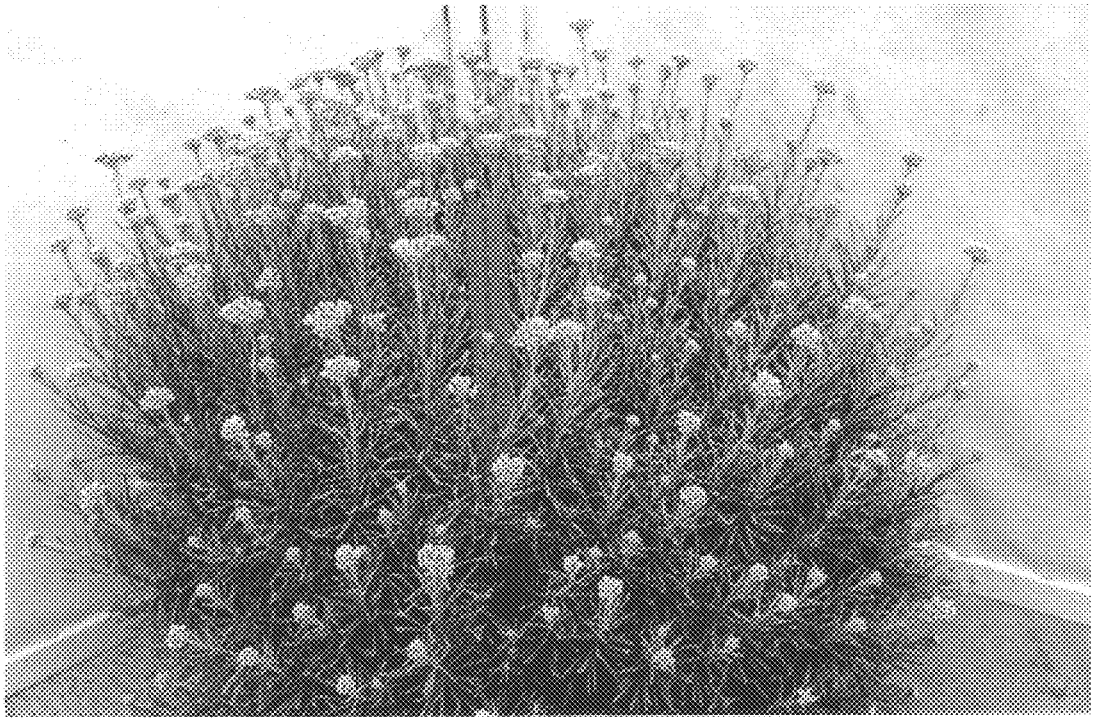

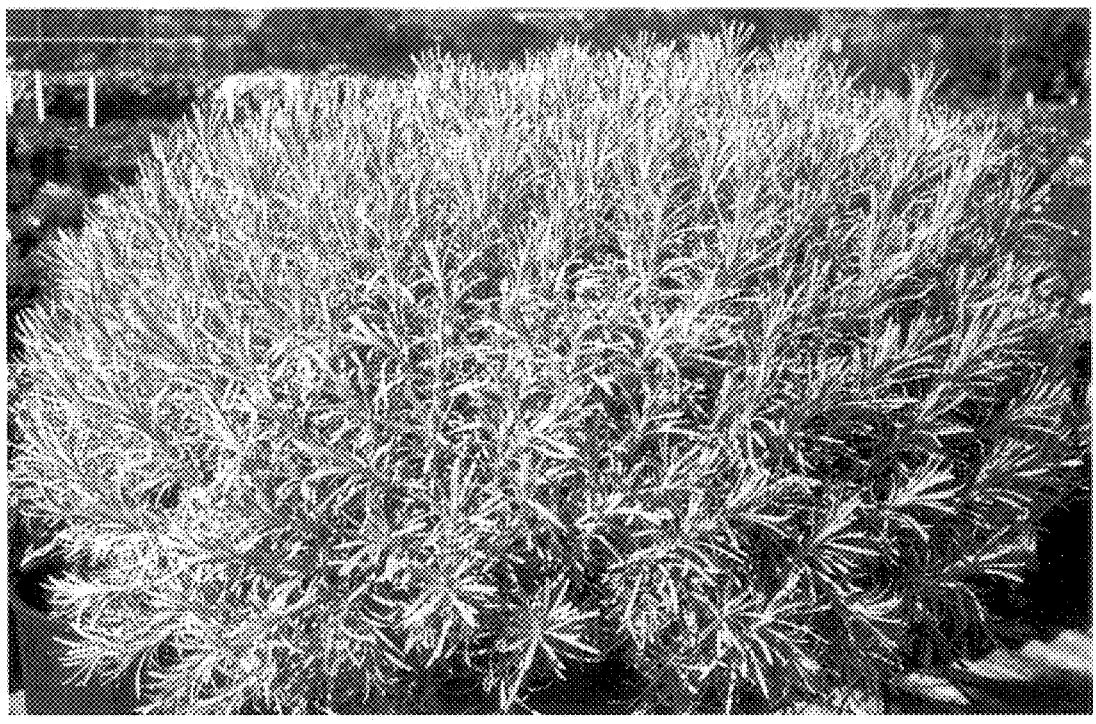

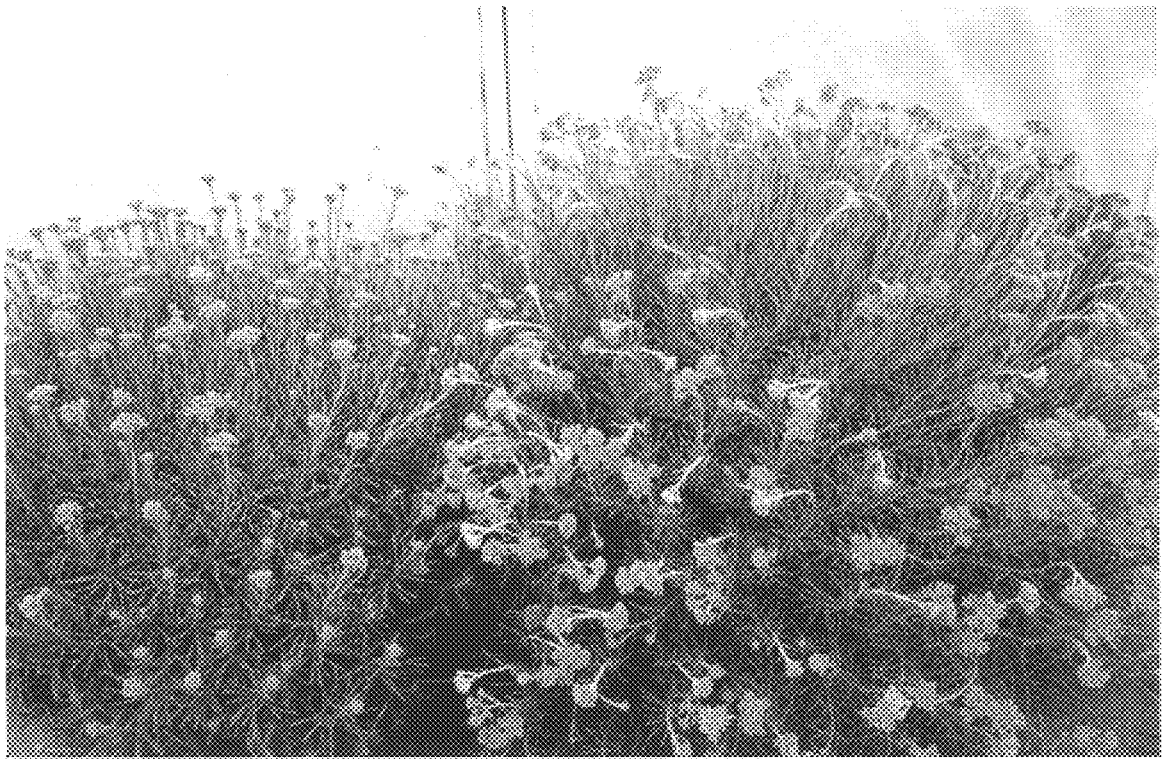

* * * * *